United States Patent [19]
Errico et al.

[11] Patent Number: 5,735,851
[45] Date of Patent: Apr. 7, 1998

[54] MODULAR POLYAXIAL LOCKING PEDICLE SCREW

[75] Inventors: Joseph P. Errico, Far Hills; Thomas J. Errico, Summit; James D. Ralph, Oakland; Steve Tatar, Montville, all of N.J.

[73] Assignee: Third Millennium Engineering, LLC, Summit, N.J.

[21] Appl. No.: 728,017

[22] Filed: Oct. 9, 1996

[51] Int. Cl.⁶ .................................................. A61B 17/70
[52] U.S. Cl. ........................................ 606/61; 606/73
[58] Field of Search .............................. 606/61, 60, 69, 606/70, 71, 72, 73, 59, 54; 623/17

[56] References Cited

U.S. PATENT DOCUMENTS

| | | | |
|---|---|---|---|
| 5,344,422 | 9/1994 | Frigg | 606/61 |
| 5,476,464 | 12/1995 | Metz-Stravenhagen et al. | 606/61 |
| 5,480,401 | 1/1996 | Navas | 606/61 |
| 5,501,684 | 3/1996 | Schlapfer et al. | 606/73 |
| 5,569,247 | 10/1996 | Morrison | 606/61 |
| 5,575,792 | 11/1996 | Errico et al. | 606/61 |
| 5,584,831 | 12/1996 | McKay | 606/61 |

Primary Examiner—Guy V. Tucker
Attorney, Agent, or Firm—Joseph P. Errica, Esq.

[57] ABSTRACT

A modular polyaxial pedicle screw and orthopaedic rod implant device including same includes a shaft portion, a cuff, a stem portion, and a rod coupling sub-assembly. The shaft portion is designed to be inserted into the pedicle, has a recess formed in its top, and includes a threading formed on the exterior surface around the recess. The stem portion is a threaded post having an enlarged ball formed at the base thereof, the ball being ideally suited to polyaxially rotate within the recess of the shaft. The cuff is a cylindrical element designed to seat around the interface of the ball portion of the stem and the recess of the shaft, initially so that the stem and shaft may polyaxially rotate relative to one another, and subsequently to hold the stem and shaft in final securement. The rod coupling sub-assembly consists of a rod coupling element which is mountable on the post portion of the stem, and a top locking nut which secures the rod coupling element to the post between the nut and the cuff. Spacer elements may be utilized which are positioned on the post between the cuff and the rod coupling element to permit axial variability on the stem in addition to the angular variability inherent in the shaft and stem interface.

12 Claims, 6 Drawing Sheets

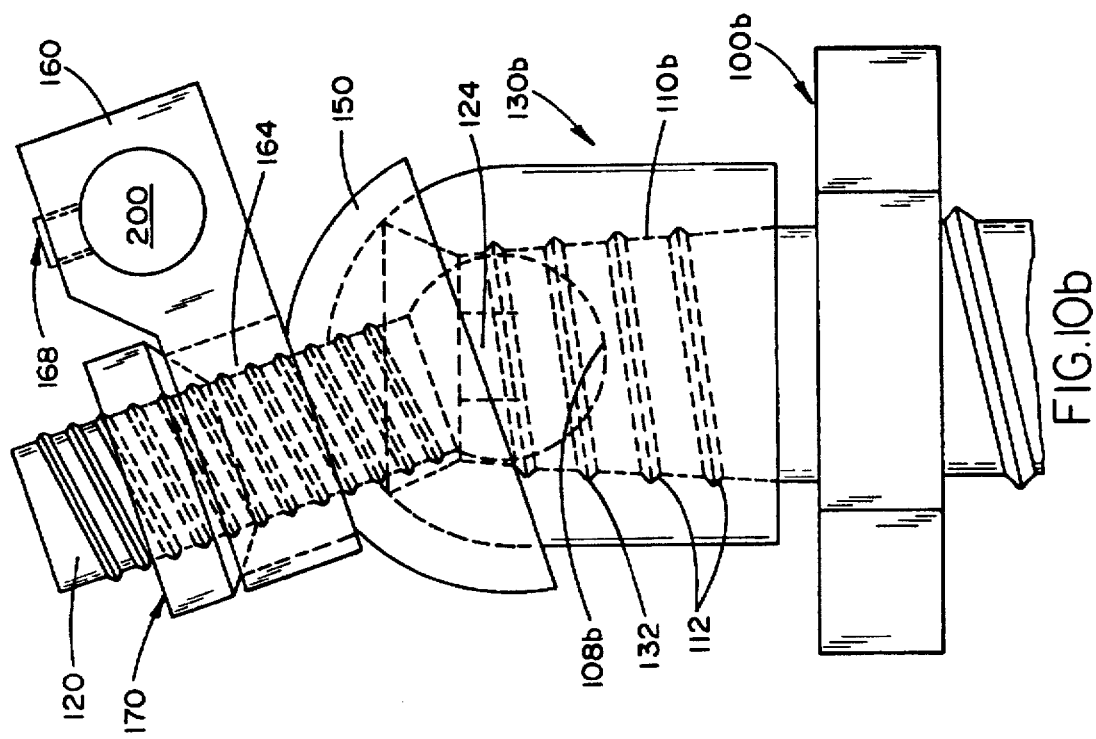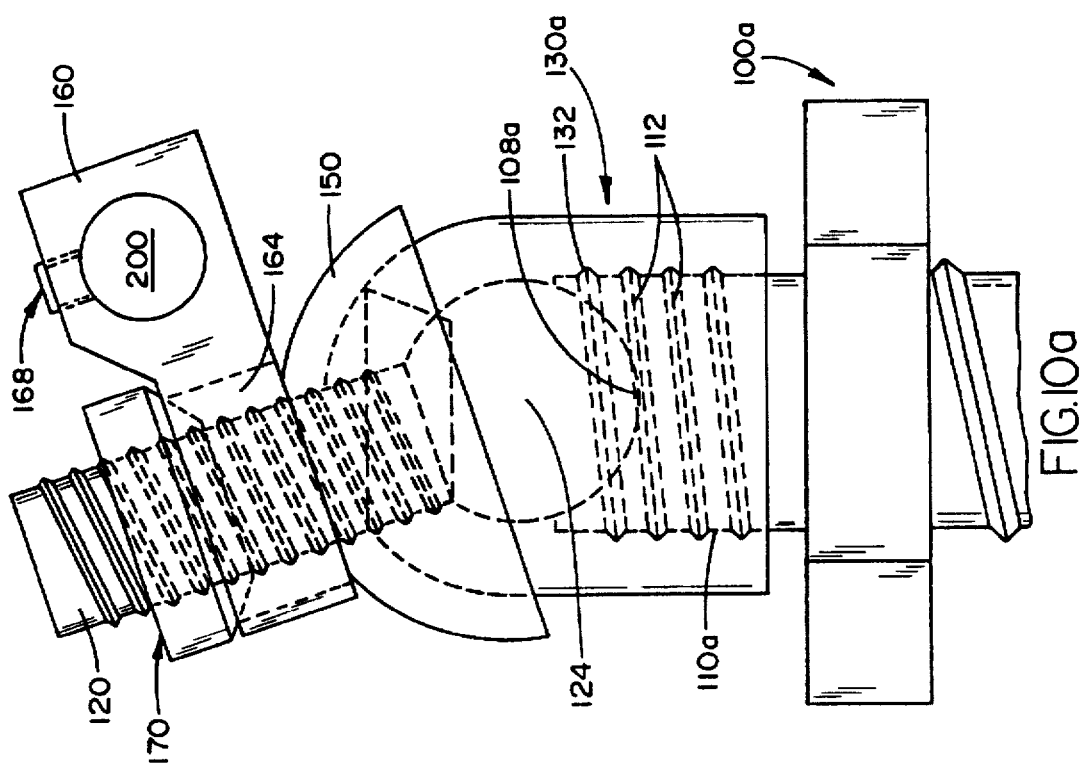

MODULAR POLYAXIAL LOCKING PEDICLE SCREW

BACKGROUND OF THE INVENTION

1. Field of the Invention

This invention relates generally to a polyaxial pedicle screw for use with orthopedic fixation systems having modular components. More particularly, the present invention relates to a screw for insertion into the vertebral bone having a shaft and a set of modular coupling elements which are polyaxially mounted thereto, via a stem member which is flexibly connected to the top portion of the shaft portion, therein enhancing the efficacy of the implant assembly by providing freedom of angulation among the rod, shaft and modular elements.

2. Description of the Prior Art

The bones and connective tissue of an adult human spinal column consists of more than 20 discrete bones coupled sequentially to one another by a tri-joint complex which consist of an anterior disc and the two posterior facet joints, the anterior discs of adjacent bones being cushioned by cartilage spacers referred to as intervertebral discs. Referring now to FIGS. 1, 2, and 3, top, side, and posterior views of a vertebral body, a pair of adjacent vertebral bodies, and a sequence of vertebral bodies are shown, respectively. The spinal cord is housed in the central canal 10, protected from the posterior side by a shell of bone called the lamina 12. The lamina 12 includes a rearwardly and downwardly extending portion called the spinous process 16, and laterally extending structures which are referred to as the transverse processes 14. The anterior portion of the spine comprises a set of generally cylindrically shaped bones which are stacked one on top of the other. These portions of the vertebrae are referred to as the vertebral bodies 20, and are each separated from the other by the intervertebral discs 22. The pedicles 24 comprise bone bridges which couple the anterior vertebral body 20 to the corresponding lamina 12.

The spinal column of bones is highly complex in that it includes over twenty bones coupled to one another, housing and protecting critical elements of the nervous system having innumerable peripheral nerves and circulatory bodies in close proximity. In spite of these complexities, the spine is a highly flexible structure, capable of a high degree of curvature and twist in nearly every direction. Genetic or developmental irregularities, trauma, chronic stress, tumors, and disease, however, can result in spinal pathologies which either limit this range of motion and/or threaten the critical elements of the nervous system housed within the spinal column. A variety of systems have been disclosed in the art which achieve this immobilization by implanting artificial assemblies in or on the spinal column. These assemblies may be classified as anterior, posterior, or lateral implants. As the classifications suggest, lateral and anterior assemblies are coupled to the anterior portion of the spine, which is the sequence of vertebral bodies. Posterior implants generally comprise pairs of rods, which are aligned along the axis which the bones are to be disposed, and which are then attached to the spinal column by either hooks which couple to the lamina or attach to the transverse processes, or by screws which are inserted through the pedicles.

"Rod assemblies" generally comprise a plurality of such screws which are implanted through the posterior lateral surfaces of the laminae, through the pedicles, and into their respective vertebral bodies. These screws are typically provided with upper portions which comprise coupling means, for receiving and securing an elongate rod therethrough. The rod extends along the axis of the spine, coupling to the plurality of screws via their coupling means. The rigidity of the rod may be utilized to align the spine in conformance with a more healthful shape.

It has been identified, however, that a considerable difficulty is associated with inserting screws along a misaligned curvature and simultaneously exactly positioning the coupling elements such that the rod receiving portions thereof are aligned so that the rod can be passed therethrough without distorting the screws. Attempts at achieving proper alignment with fixed screws is understood to require increased operating time, which is known to enhance many complications associated with surgery. Often surgical efforts with such fixed axes devices cannot be achieved, thereby rendering such instrumentation attempts entirely unsuccessful.

The art contains a variety of attempts at providing instrumentation which permit enhanced freedom for the surgeon with respect to aligning the screw and the rod, however, most are complex, inadequately reliable, and lack long-term durability. In addition, most generally lack the feature of being constructed to suit the specific anatomical requirements of every patient's spine. In particular, the Isola(™) system, which is produced by Acromed, suffers from many of these failures in as much as it does not provide the surgeon to freely angulate the rod coupling means of the screw to meet the rod. More specifically, as illustrated in FIGS. 4 and 5, the Isola system consists of a shaft portion which is to be inserted into the patient's pedicle, the shaft having a threaded stem portion rigidly extending upwardly from the top of the shaft portion. (The interface of the shaft portion and the stem portion includes a hexagonally shaped annulus for engagement with a torque wrench to permit insertion.) Once the shaft and stem have been inserted, the surgeon threadably advances a number of spacer elements onto the stem portion (the spacer elements are threaded washers, some having a non-uniform thickness so as to provide an angular bias or tilt to the overall construct). Next the surgeon places the rod coupling means (which is slideably advanced axially onto the rod) onto the stem. The rod coupling means includes an elongated slot so that the specific position of the rod coupling means relative to the stem may be varied slightly. Once fully positioned, the surgeon secures the assembly together with a top locking nut.

While being modular so as to provide limited variability in the construct, the Isola system has very limited ability to angulate (the stem is rigidly connected to the shaft portion), and what limited ability to angulate that it has entails the use of a plethora of non-uniformly thick spacer elements which are tedious to use in a surgical environment.

It is, therefore, the principal object of the present invention to provide a pedicle screw and coupling element assembly which provides a polyaxial freedom of implantation angulation with respect to rod reception.

In addition, it is an object of the present invention to provide such an assembly which comprises a reduced number of elements, and which correspondingly provides for expeditious implantation.

Accordingly it is also an object of the present invention to provide an assembly which is reliable, durable, and provides long term fixation support.

Other objects of the present invention not explicitly stated will be set forth and will be more clearly understood in conjunction with the descriptions of the preferred embodiments disclosed hereafter.

SUMMARY OF THE INVENTION

The preceding objects of the invention are achieved by the present invention which is a polyaxial modular locking pedicle screw assembly for use with rod stabilization and immobilization systems in the spine. More particularly, the polyaxial screw assembly of the present invention comprises: a threaded shaft portion for insertion into the pedicle, the top of shaft portion including a bowl-shaped socket and a second threading; a stem portion having a threading, corresponding to the second threading, for receiving spacer elements and/or a rod coupling element thereon, the bottom of said stem portion including a ball (semi-spherical section); and a cylindrical locking cuff which is mounted about the top of the shaft and the bottom of the stem to secure the ball of the stem in the bowl-shaped socket of the shaft.

More particularly, with respect to the shaft portion, the elongate shank portion of the shaft includes the threading of a bone screw (standard or otherwise, but suited for proper purchase of the bone). The uppermost portion of the shaft comprises a bowl-shaped recess which forms a socket. This socket portion may be greater or less than a fully hemispherical recess. In an embodiment in which the socket is greater than a hemisphere, axial slots need to be provided so that the ball may be slipped into the socket. A small hexagonal bore may be disposed in the based of the bowl-shaped socket, coaxial with the shaft, so that a screw driving device (allen wrench, etc.) may be utilized to insert the shaft into the bone. Alternatively, a widened annular portion of the shaft, disposed between the two threadings may be hexagonal so as to permit the use of a torque wrench or other surgical tool. The axial surface of the shaft at the top (socket) end includes the second threading, for receiving and locking the cuff element thereto.

The stem comprises an elongate post portion having an enlarged ball (having a larger diameter than the post portion) formed at the bottom thereof; the enlarged ball having substantially the same radius of curvature as the bowl-shaped socket portion of the shaft. Therefore, when the ball is initially placed in the bowl-shaped socket, the stem may be positioned in a variety of different angulations relative to the axis of the shaft portion (through a polyaxial range of configurations from coaxial to substantially non-coaxial).

The securing cuff comprises a hollow cylindrical body, having a threading on the bottom half (halves being defined relative to the through axis) of the interior surface thereof. This threading is designed to mate with the threading on the uppermost portion of the shaft element. The upper half of the interior surface of the cuff may comprise a semi-spherical taper when used in conjunction with a shaft which has a socket which is less than hemispherical. This taper forms an open ended socket. In an alternative embodiment, to be used with a shaft having a socket which is greater than a hemisphere, the top end of the cuff need not be tapered on the inside. In either case, however, the inner diameter of the open end of the top of the cuff is larger than the diameter of the post portion of the stem, but more narrow than the diameter of the ball formed at the bottom end of the stem. During assembly, the stem and shaft portions are initially held coaxial, with the ball of the stem in the socket of the shaft portion, while the securing cuff is advanced down along the post portion of the stem until the threadings of the cuff and the uppermost exterior surface of the shaft engage. Prior to final tightening, the stem and shaft are thereby held together by the cuff, but each may be angulated relative to the other by virtue of the ball and socket interface. (The total range of angulation is established by the relative diameters of the ball, the post, and the opening at the top of the cuff.) Complete tightening of the cuff, however, causes the ball to be crushed into the socket of the shaft (and the tapered interior of the upper portion of the cuff), thereby preventing any further motion.

A portion of the exterior of the cuff comprises a hexagonally angled surface contour, such that the cuff may be easily engaged by a torque wrench. (It shall be understood that any one of a variety of such surface contours or other means may be employed equivalently.) The upper exterior of the cuff, however, is rounded (with a constant radius of curvature) so that it provides a curvate profile. This permits the secure engagement of similarly rounded spacer elements relative to the top of the cuff element independent of the angular orientation of the post portion of the stem relative to the cuff and shaft (the cuff and shaft remain coaxial).

More particularly, inasmuch as it is still desirable to permit variable positioning of the rod coupling means along the axis of the stem, in addition to the angular variability provided by the polyaxial shaft-stem-cuff assembly, spacer elements may also be utilized. The spacers are annular elements having a diameter which is equivalent to that of the post portion (and are preferrably threaded). The bottom surfaces of the spacer elements are concave, having a radius of curvature equal to that of the upper surface of the cuff. As stated above, this mutual contour permits the spacer to seat securely against the cuff independent of the angulation of the stem. The upper surface of the spacer element is convex, having an equivalent radius of curvature, such that multiple spacers may be nested.

It shall be understood that the advancing the spacer elements downwardly on the stem, and into contact with the cuff, and subsequent tightening, causes an increase in the total locking force applied to the ball in the socket (the ball is pulled into tighter contact with the socket-shaped interior of the cuff). In order to threadably advance the spacer elements easily, the outer lateral surface of the elements are contoured so as to be engageable by a torque wrench; e.g., having a hexagonal shape.

The rod coupling element of this assembly comprises a flat portion having an elongate hole therethrough for coupling to the stem, and a tubular portion which may be slideably advanced along the rod into the proper position. Once in the proper position, the rod coupling means is locked to the rod by a set screw in order to prevent further movement relative to the rod. The elongate hole in the flat portion is elongate in nature so that distance from the rod to the stem may be varied. This element further includes the concave conformation on the underside thereof so that it may nest securely on the upper surface of either a spacer or directly on the cuff (in the case wherein no spacer is used).

The first step in the process of implanting this assembly is to pre-drill the appropriate site in the pedicle to receive the shaft. The shaft is then driven into the vertebral body. The cuff is then advanced down the stem portion until it reaches the ball portion. The ball is then placed into the socket of the shaft, and the threadings on the top of the shaft and on the interior of the cuff are engaged. The stem is then angulated into the appropriate position, and the cuff is locked down, thereby securing the stem relative to the shaft. The rod coupling element is then slideably advanced along the rod into the appropriate position, and the stem placed in the elongate hole thereof. The set screw of the rod coupling element is engaged to lock thereto. (Spacers are threadably advanced onto the stem prior to the insertion of the stem through the elongate hole, if it is determined that they are necessary.) Once the assembly has been properly set, the top locking nut is advanced downwardly along the stem and into position against the top of the rod coupling element, thereby preventing any lateral or axial movement of the stem within the elongate hole.

Multiple screw and coupling element assemblies are generally necessary to complete the full array of anchoring sites for the rod immobilization system, however, the screw and coupling element assembly of the present invention is designed to be compatible with alternative rod systems so that, where necessary, the present invention may be employed to rectify the failures of other systems the implantation of which may have already begun.

BRIEF DESCRIPTION OF THE FIGURES

FIGS. 10a and 10b are side views of two fully assembled modular polyaxial pedicle screws of the present invention.

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 2:
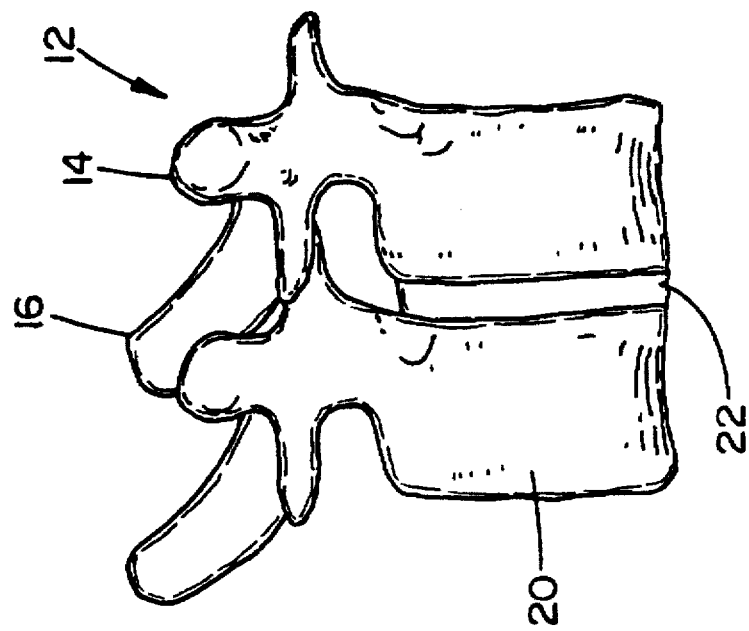
FIG. 2 is a side view of a pair of adjacent vertebrae of the type shown in FIG. 1.
Figure 1:
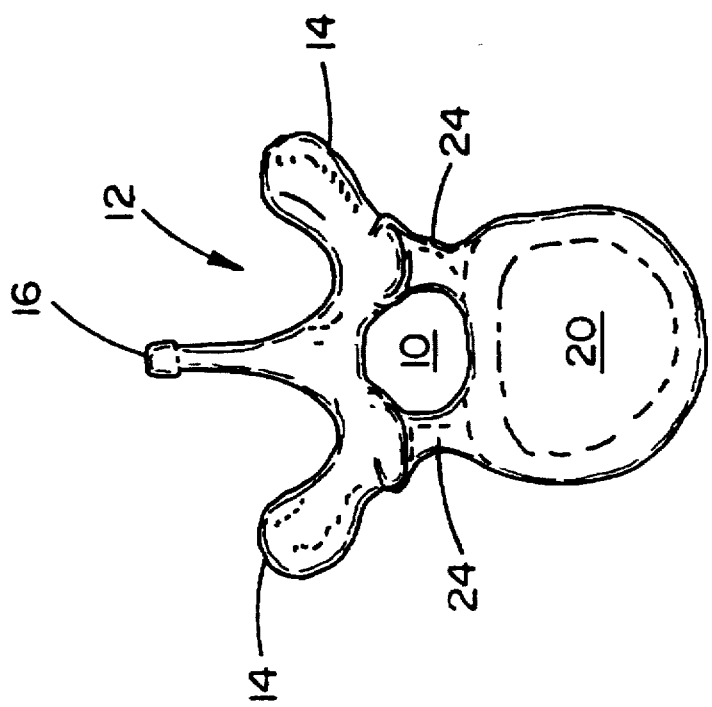
FIG. 1 is a top view of a human vertebra, which is representative of the type for which the present invention is useful for coupling thereto a rod apparatus.
Figure 3:
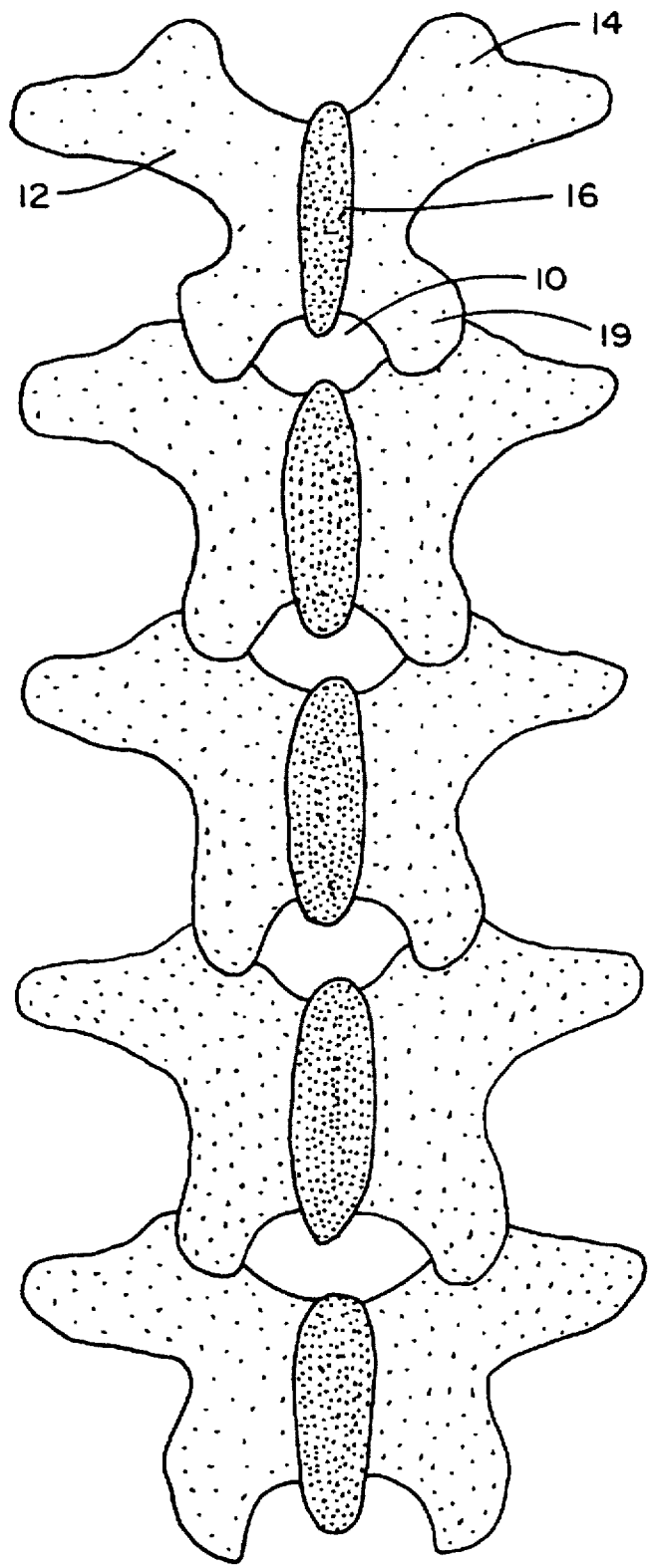
FIG. 3 is a posterior view of a sequence of vertebrae of the type shown in FIGS. 1 and 2.
Figure 4A:
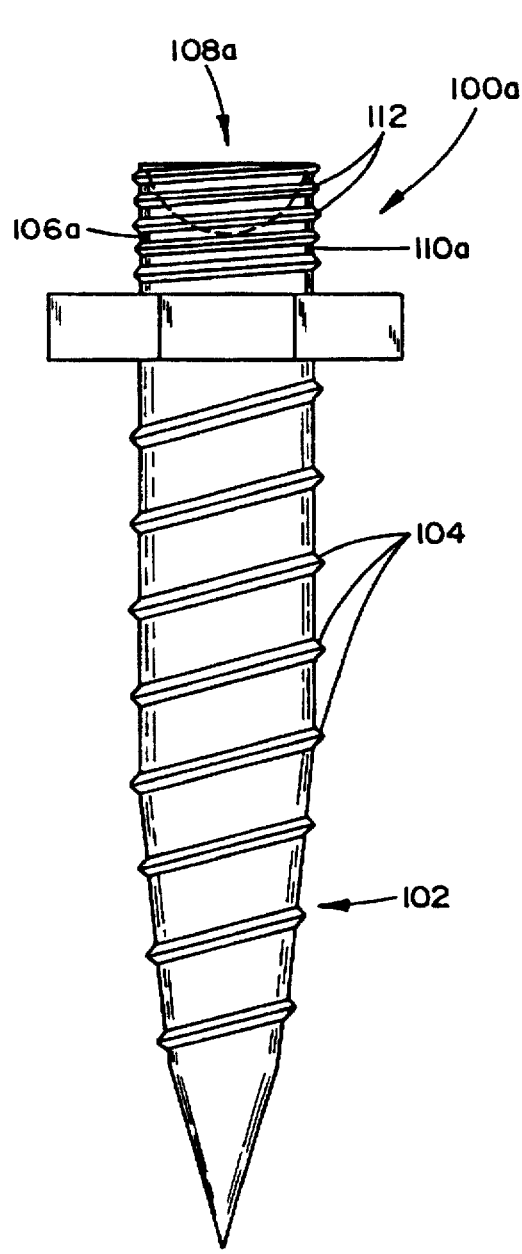
FIGS. 4a and 4b are side cross section views of alternative threaded shafts which are aspects of the present invention.
Figure 4B:
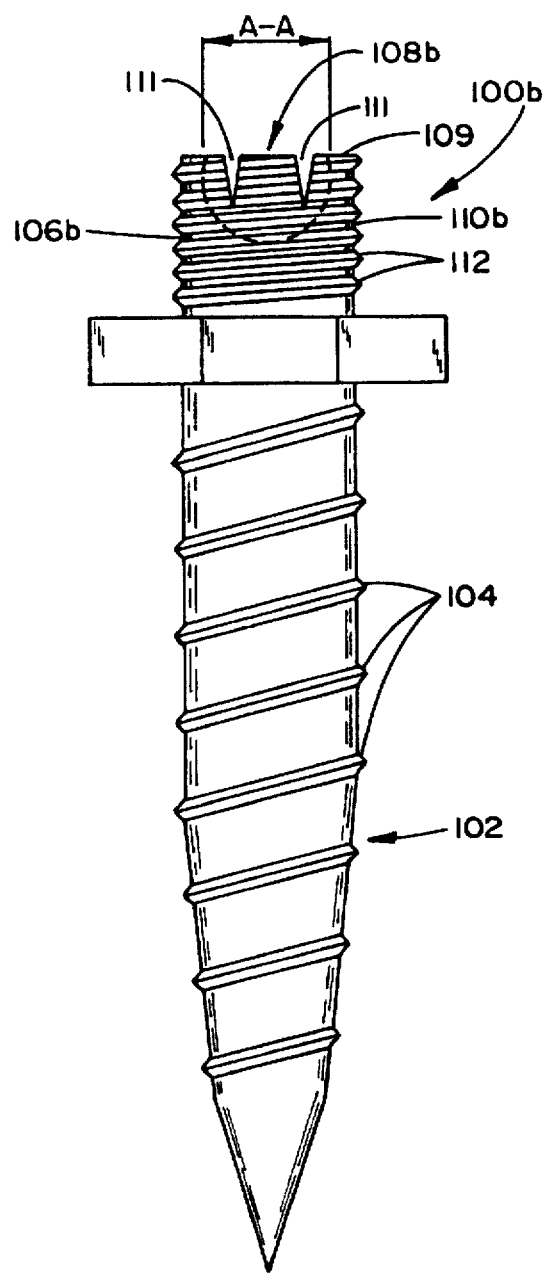

More particularly, referring now to FIGS. 4a and 4b, the alternative modular polyaxial pedicle screws of the present invention first comprises a threaded shaft portion 100a,100b which is inserted into the pedicle. Both shafts 100a,100b include a lower shank portion 102 which include a bone screw threading 104. (This threading 104 may be standard or otherwise, but is in any case suited for necessary purchase of bone.) Specifically with respect to the illustration 4a, the top 106a of the shaft 100a comprises a bowl-shaped recess 108a which forms a socket. This socket 108a comprises less than a hemispherical section. Alternatively, as shown in FIG. 4b, the top 106b of the shaft 100b may comprise a socket 108b which is greater than a hemispherical section. In such a socket 108b, the upper lip 109 thereof should include at least one axial slot 111 which extends below the maximum diameter A—A, and which may expand and contract in accordance with the application of a radial force on the upper lip 109.

In both alternatives, the axial surfaces of the upper ends 110a,110b of the shafts 100a,100b (around the sockets 108a,108b) include a second threading 112. A widened hexagonal annulus 114, which is integrally formed with the shaft 100a,100b, and is disposed between the threaded shank 102 and upper portions 110a,110b, is provided so that a suitable torque wrench may be employed to drive the shaft 100a,100b into the vertebral body through the pedicle.

Figure 5:
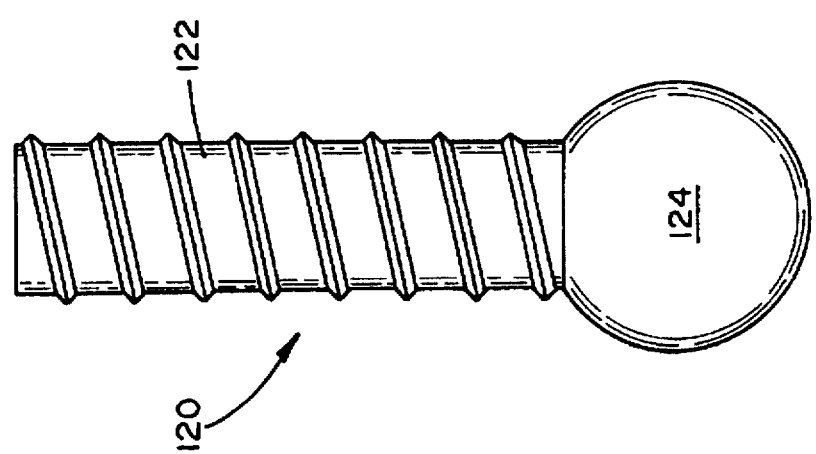
FIG. 5 is a side view of a stem portion, having a ball formed at the bottom thereof, which is an aspect of the present invention.

Referring now to FIG. 5, a stem portion 120 is shown in a side view. More specifically, the stem 120 comprises an elongate threaded post portion 122 and an enlarged ball 124. The ball 124 has a larger diameter than the post 122. The ball 124 has substantially the same radius of curvature as the bowl-shaped socket 108 portion of the shaft 100. This mutual dimension permits the ball 124 to rotate freely in the socket 108 once the ball 124 is placed therein, thus permitting the stem 120 to be angulated relative to the shaft 100 (through a polyaxial range from coaxial to substantially non-coaxial).

Figure 6B:
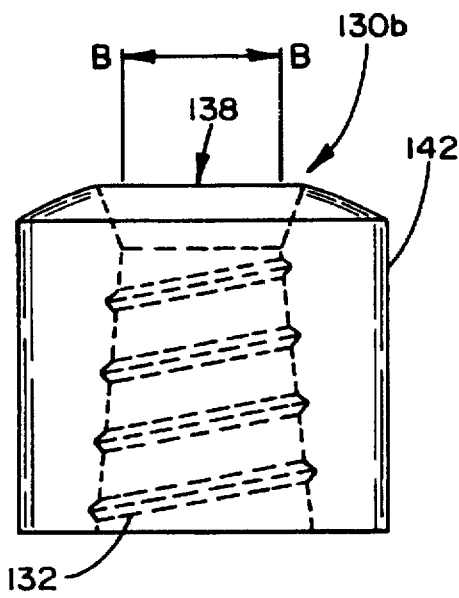
FIGS. 6a and 6b are side cross section views of alternative cuffs of the present invention.
Figure 6A:
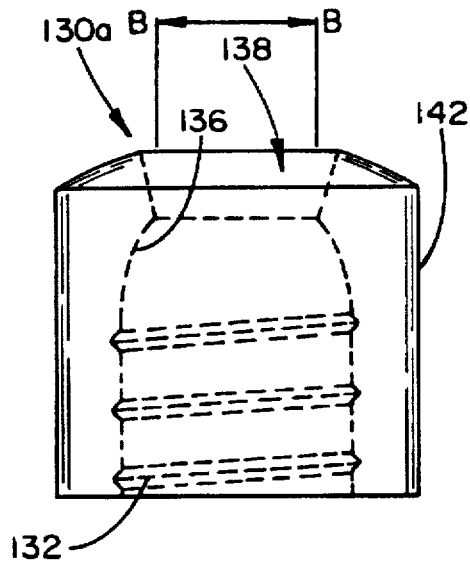

Referring to FIGS. 6a and 6b, the mutual engagement of the shafts 100a,100b with the stem 120 is provided by corresponding cuffs 130a,130b, shown in side cross section views. The cuffs 130a,130b are each hollow cylinders and have a threading 132 on the bottom half of the interior surface 134 thereof. This threading 132 is designed to mate with the threading 112 on the uppermost portion 110a,110b of the shaft element 100a,100b. With respect to the embodiment of the cuff 130a which is used in conjunction with the shaft 100a having a socket with a socket defining less than a hemisphere, the upper half of the interior surface 136 of the cuff 130a comprises a semi-spherical taper, which forms an open ended socket. Alternatively, the embodiment which is to be utilized with the shaft 100b having a socket 108b which defines greater than a hemisphere, has no internal taper at the upper end, however, the lower threaded portion may include a reverse taper, i.e. narrower at the top, in order to provide an inwardly directed radial force onto the upper lip 109. In each embodiment 130a,130b, the inner diameter B—B of the open end 138 of the top of the cuff 130a,130b is larger than the diameter of the threaded post portion 122 of the stem 120, but more narrow than the diameter of the ball 124.

During assembly, the stem 120 and shaft 100a,100b portions are initially held coaxial, with the ball 124 of the stem 120 in the socket 108a,108b of the shaft 100a,100b (the ball 124 being snapped into the socket 108b by applying a downward force whereby the at least one slot 111 expands), while the securing cuff 130a,103b is advanced down along the post portion of the stem until the threadings 132,112 of the cuff 130a,130b and the uppermost exterior surface 110a,110b of the shaft, respectively, engage. Prior to final tightening, the stem 120 and shaft 100a,100b are thereby loosely held together by the cuff 130a,130b, respectively, but each may be angulated relative to the other by virtue of the ball 124 and socket 108a,108b interface. The total range of angulation is established by the relative diameters of the ball 124, the post 122, (the upper lip 109 of the socket 108b), and the opening 138 at the top of the cuff. Complete tightening of the cuff 130a,130b, however, causes the ball 124 to be crushed into the socket 108a,108b, thereby preventing any further motion.

A portion of the exterior 140 of the cuff 130a,130b comprises a hexagonally angled surface contour, such that the cuff 130a,130b may be easily engaged by a torque wrench. In addition, the upper exterior 142 of the cuff 130a,130b, however, is rounded (with a constant radius of curvature) so that it provides a curvate profile. This permits the secure engagement of similarly rounded spacer elements (see FIG. 7, and related description hereinbelow) relative to the top of the cuff 130a,130b independent of the angular orientation of the post 122 of the stem 120 relative to the cuff 130a,130b and shaft 100a,100b.

Figure 7:
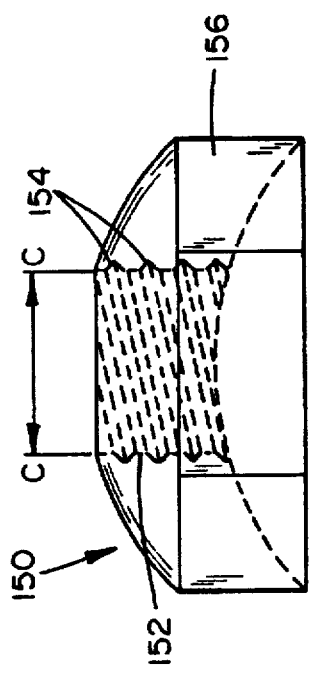
FIG. 7 is a side cross section view of a spacer element which is an aspect of the present invention.

More particularly, with reference to FIG. 7, inasmuch as it may be desirable to vary the axial position of the rod coupling means (see FIG. 8, and related description hereinbelow) along the post 122, spacer elements 150 are provided. The spacers 150 are annular elements having an inner diameter C—C which is equivalent to that of the post 122. In the illustrated embodiment, the inner surface 152 includes a threading 154 which is engageable with the threading of the post 122. (It is not necessary for the spacers 150 to be threaded, however, such a threading may provide additional downward force on the cuff 130a,130b to further secure the locking of the stem 120 and the shaft 100a,100b.) The bottom surface of the spacer 150 is concave, having a radius of curvature equal to that of the tapered upper portion 142 of the cuff 130a,130b. This mutual contour permits the spacer 150 to seat securely against the cuff 130a,130b independent of the angulation of the stem 120. The upper surface 142 of the spacer 150 is convex, having an equivalent radius of curvature, such that multiple spacers 150 may be nested. In order that the threaded spacer 150 may be advanced easily along the threaded post 122, the outer lateral surface 156 is contoured so as to be engageable by a torque wrench; e.g., having a hexagonal shape.

Figure 8:
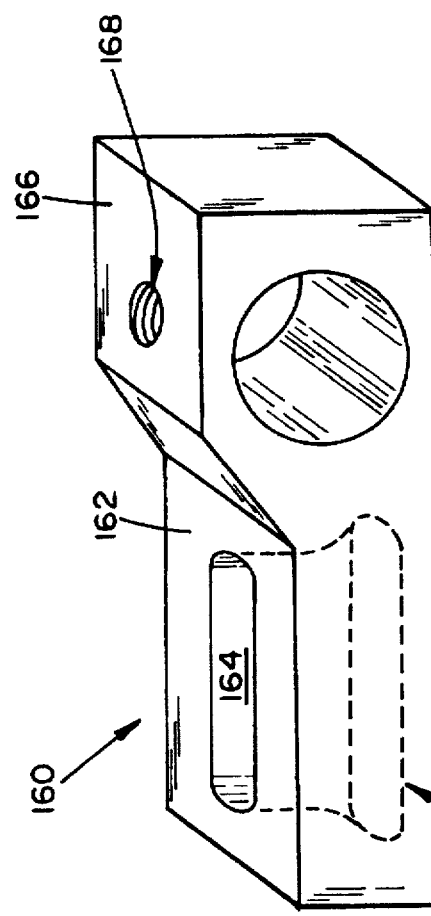
FIG. 8 is a perspective view of a rod coupling element which is an aspect of the present invention.

Referring now to FIG. 8, the rod coupling element 160 of this assembly comprises a flat portion 162 having an elongate hole 164 therethrough for coupling to the stem 120. The elongate hole 164 has a width equal to that of the post 122, but is elongated to permit variable lateral placement of the post 122 relative to the rod 200. The edge (not seen in this illustration) of the elongated hole 164, on the underside of the flat portion, is concavely tapered so as to ideally receive the curvate upper portion of the spacer 150 or the cuff 130a,130b.

The rod coupling element 160 further includes a tubular portion 166, the axis of the tube is substantially perpendicular to the elongated axis of the hole 164. The rod coupling element 160 is positioned on the rod 200 by slideably advancing it therealong. Once in the proper position, the rod coupling element 160 is locked to the rod 200 by a set screw 168 in order to prevent further movement relative to the rod. In addition, this element 160 further includes a concave underside conformation 170 such that it may nest securely on the upper surface of either a spacer 150 or directly on the cuff 130a,130b (in the case wherein no spacer 150 is used).

Figure 9:
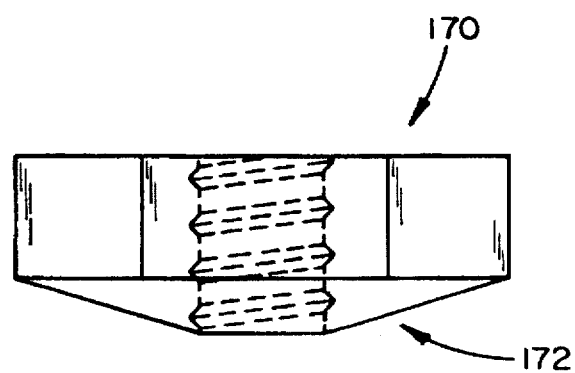
FIG. 9 is a side cross-sectional view of the top locking nut of the present invention.

Referring to FIG. 9, a top locking nut 170 is utilized to lock the rod coupling element 160 onto the post 122. More particularly, the top locking nut 170 has a bottom surface 172 which is ideally suited to engage and hold the post 122 and the rod coupling element 160 from axial or lateral movement. Specifically, the top locking nut 170 is designed to apply a downward pressure which is sufficient to lock the cuff 130a,130b into the tapered curvate edge of the elongate hole 164 such that the friction locking force of the spacer 150 or cuff 130a,130b thereagainst is sufficient to hold the rod coupling element 160 from lateral, or axial, movement.

Referring now to FIGS. 10a and 10b, the steps of implanting this assembly is described. First, a hole is pre-drilled in the appropriate site in the pedicle in order to receive the shaft 100a,100b. The shaft 100a,100b is then driven into the vertebral body. The cuff 130a,130b is then advanced down the stem 120 until it reaches the ball 124. The ball 124 is then placed (or snapped) into the socket 108a,108b, and the threadings 112,132 on the upper portion 110a,110b of the shaft 100a,100b and on the interior of the cuff 130a,130b, respectively, are engaged. The post 122 is then angulated into the appropriate position, and the cuff 130a,130b is locked down, thereby securing the stem 120 relative to the shaft 130a,130b. (The ball 124 is crush locked between the cuff 130a and the socket 108a. Alternatively, the ball 124 is crushed into the socket 108b by virtue of the socket itself being collapsed onto the ball 124.) If necessary, spacers 150 are positioned above the cuff 130a,130b on the post 122. The rod coupling element 160 is then slideably advanced along the rod 200 into the appropriate position, and the post 122 is placed in the elongate hole 164 thereof. The set screw 168 of the rod coupling element 160 is engaged to lock it to the rod 200. Finally the top locking nut 170 is advanced downwardly along the post 122 and into position against the rod coupling element 160, thereby preventing any lateral or axial movement of the post 122 within the elongate hole 164.

A complete posterior rod implant system includes at least two, and generally four or more, screw assemblies. However, this assembly, as set forth above, may also be used in conjunction with other screw assemblies in the art wherein there is an immediate need for the beneficial properties of this assembly to correct deficiencies in the other assemblies. Therefore, it is anticipated that this modular polyaxial pedicle screw may be used individually, or in conjunction with others.

While there has been described and illustrated embodiments of a modular polyaxial pedicle screw assembly for use with posterior spinal rod implantation apparatus, it will be apparent to those skilled in the art that variations and modifications are possible without deviating from the broad spirit and principle of the present invention. The present invention shall, therefore, be limited solely by the scope of the claims appended hereto.

We claim:

1. A modular polyaxial pedicle screw assembly, comprising:

a bone screw having a shaft portion and an upper portion having a curvate socket which is coaxial with said shaft portion and which defines a volume having a constant radius of curvature and which is less than a hemisphere formed therein and a threading disposed on the upper circumferential surface of said upper portion;

a stem having an upper post portion and a lower ball portion, the ball portion having a diameter which has the same radius of curvature as the curvate socket of the bone screw and larger than the upper post portion, and said ball portion being shaped to nest and initially rotate in said curvate socket;

a cuff having a hollow cylindrical body having an opening in a top thereof having a diameter greater than that of the upper post portion and less than that of the ball portion, and a threading on a lower interior surface thereof, which threading is coaxial with said opening in said top and is mateable with said threading on said upper circumferential surface of said upper portion of said screw, and such that prior to complete securing of the cuff on the upper portion the stem may polyaxially rotate relative to the shaft with the post portion extending through the opening in the top of the cuff through a range of orientations including orientations which are coaxial and non-coaxial relative to the cuff and bone screw, and such that by complete securing of the cuff on the upper portion the ball portion is crush locked in the curvate socket, thereby preventing further motion of the post relative to the shaft; and means for coupling a rod to the stem.

2. A modular polyaxial pedicle screw assembly, comprising:

a shaft having a curvate socket formed in a top thereof, said socket having a curvate surface of a constant radius of curvature and defining a volume greater in extent than a hemisphere, said socket further having at least one axial slot formed therein and extending axially downward from said top to a position which is lower than the maximum diameter of the recess, and a threading disposed on the upper circumferential surface thereof;

a stem having an upper post portion and a lower ball portion, the ball portion being shaped to nest and initially rotate in said curvate socket;

a cuff having a hollow cylindrical body and a threading on a lower interior surface thereof which interior surface is tapered upwardly and radially inwardly, and which threading is mateable with said threading on said upper circumferential surface of said shaft, and an opening in a top thereof having a diameter greater than that of the upper post portion and less than that of the ball portion, such that prior to complete securing of the cuff on the shaft the stem may polyaxially rotate relative to the shaft through a range of orientations including coaxial and non-coaxial ones, and such that by complete securing of the cuff on the shaft the ball portion is crush locked in the curvate socket, thereby preventing further motion of the stem relative to the shaft; and means for coupling a rod to the stem.

3. The assembly as set forth in claim 2, wherein the shaft includes a second threading disposed on a lower circumferential surface thereof.

4. A modular polyaxial pedicle screw assembly, comprising:

a shaft having a curvate socket formed in the top thereof and a threading disposed on the upper circumferential surface thereof and an annulus portion integrally formed therewith which is positioned beneath the threaded upper circumferential portion, said annulus having a hexagonal outer conformation;

a stem having an upper post portion and a lower ball portion, the ball portion having a larger diameter than the upper post portion, and said ball portion being shaped to nest and initially rotate in said curvate socket;

a cuff having a hollow cylindrical body and a threading on a lower interior surface thereof which threading is mateable with said threading on said upper circumferential surface of said shaft, and an opening in a top thereof having a diameter greater than that of the upper post portion and less than that of the ball portion, such that prior to complete securing of the cuff on the shaft the stem may polyaxially rotate relative to the shaft through a range of orientations including coaxial and non-coaxial ones, and such that by complete securing of the cuff on the shaft the ball portion is crush locked in the curvate socket, thereby preventing further motion of the stem relative to the shaft; and means for coupling a rod to the stem.

5. The assembly as set forth in claim 4, wherein said upper post portion comprises a surface threading.

6. The assembly as set forth in claim 4, wherein said cuff includes an external circumferential surface portion which defines a hexagonal conformation.

7. The assembly as set forth in claim 4, wherein said cuff includes an upper interior surface which is axially tapered so as to define a rounded interior cupping surface having the same radius of curvate as the recess.

8. A modular polyaxial pedicle screw assembly, comprising:

a shaft having a curvate socket formed in the top thereof and a threading disposed on the upper circumferential surface thereof;

a stem having an upper post portion and a lower ball portion, the ball portion having a larger diameter than the upper post portion, and said ball portion being shaped to nest and initially rotate in said curvate socket;

a cuff having a hollow cylindrical body and a threading on a lower interior surface thereof which threading is mateable with said threading on said upper circumferential surface of said shaft, and an opening in a top thereof having a diameter greater than that of the upper post portion and less than that of the ball portion, such that prior to complete securing of the cuff on the shaft the stem may polyaxially rotate relative to the shaft through a range of orientations including coaxial and non-coaxial ones, and such that by complete securing of the cuff on the shaft the ball portion is crush locked in the curvate socket, thereby preventing further motion of the stem relative to the shaft and an upper exterior surface and a top exterior surface which are mutually axially tapered to exhibit a rounded conformation;

means for coupling a rod to the stem; and at least one spacer element disposed between the cuff and the means for coupling a rod to said stem, wherein said at least one spacer element comprises a washer having a concave lower surface and a convex upper surface, said concavity and convexity of said upper and lower surfaces having the equivalent absolute curvature as said upper exterior and top surfaces of said cuff.

9. The assembly as set forth in claim 8, wherein said upper post portion of said stem includes an exterior surface threading and wherein said interior circumferential surface of said at least one spacer element also includes a threading.

10. The assembly as set forth in claim 9, wherein said at least one spacer element comprises an exterior circumferential conformation which defines a hexagonal shape.

11. A modular polyaxial pedicle screw assembly, comprising:

a shaft having a curvate socket formed in the top thereof and a threading disposed on the upper circumferential surface thereof;

a stem having an upper post portion and a lower ball portion, the ball portion having a larger diameter than the upper post portion, and said ball portion being shaped to nest and initially rotate in said curvate socket;

a cuff having a hollow cylindrical body and a threading on a lower interior surface thereof which threading is mateable with said threading on said upper circumferential surface of said shaft, and an opening in a top thereof having a diameter greater than that of the upper post portion and less than that of the ball portion, such that prior to complete securing of the cuff on the shaft the stem may polyaxially rotate relative to the shaft through a range of orientations including coaxial and non-coaxial ones and such that by complete securing of the cuff on the shaft the ball portion is crush locked in the curvate socket, thereby preventing further motion of the stem relative to the shaft;

a rod coupling element which is mountable on said upper post portion of said stem, and a top locking nut securable to said upper post portion, above said rod coupling element, thereby securing said rod coupling element between the top locking nut and said cuff.

12. An orthopaedic implant device for use in a spine, comprising:

at least one rod positioned in parallel with the elongate axis of the spine;

a plurality of pedicle screw assemblies for securely coupling said at least one rod to said spine, at least one of said pedicle screws being a modular polyaxial pedicle screw including a shaft having a curvate socket formed in the top thereof and a threading disposed on the upper circumferential surface thereof, a stem having an upper post portion and a lower ball portion, the ball portion having a larger diameter than the upper post portion, and said ball portion being shaped to nest and initially rotate in said curvate socket, a cuff having a hollow cylindrical body and a threading on a lower interior surface thereof which threading is mateable with said threading on said upper circumferential surface of said shaft, and an opening in a top thereof having a diameter greater than that of the upper post portion and less than that of the ball portion, such that prior to complete securing of the cuff on the shaft the stem may polyaxially rotate relative to the shaft through a range of orientations including coaxial and non-coaxial ones, and such that by complete securing of the cuff on the shaft the ball portion is crush locked in the curvate socket, thereby preventing further motion of the stem relative to the shaft, a rod coupling element which is mountable on said upper post portion of said stem, and a top locking nut, securable to said upper post portion, above said rod coupling element, thereby securing said rod coupling element between the top locking nut and said cuff.

* * * * *